(12) United States Patent
Gerntholtz (10) Patent No.: US 7,840,421 B2
(45) Date of Patent: Nov. 23, 2010

(54) INFECTIOUS DISEASE SURVEILLANCE SYSTEM

(76) Inventor: Otto Carl Gerntholtz, B302 Sea Spray, Marine Drive, Bloubergrand, 7441 (ZA)

(*) Notice: Subject to any disclaimer, the term of this patent is extended or adjusted under 35 U.S.C. 154(b) by 1352 days.

(21) Appl. No.: 10/209,542

(22) Filed: Jul. 31, 2002

(65) Prior Publication Data

US 2004/0024612 A1 Feb. 5, 2004

(51) Int. Cl.
| | |
|---|---|
| G06Q 10/00 | (2006.01) |
| G06Q 50/00 | (2006.01) |
| A61B 5/00 | (2006.01) |
| G06F 19/00 | (2006.01) |

(52) U.S. Cl. ............................................. 705/3; 705/2
(58) Field of Classification Search .................... 705/2, 705/3, 4
See application file for complete search history.

(56) References Cited

U.S. PATENT DOCUMENTS

| | | | |
|---|---|---|---|
| 5,018,067 A | 5/1991 | Mohlenbrock et al. . | 364/431.02 |
| 5,199,439 A | 4/1993 | Zimmerman et al. ........ | 128/670 |
| 5,255,187 A | 10/1993 | Sorensen ............... | 364/413.02 |
| 5,619,991 A | 4/1997 | Sloane ........................ | 128/630 |
| 5,666,953 A | 9/1997 | Wilk ....................... | 128/653.1 |
| 5,704,371 A | 1/1998 | Shepard ...................... | 128/897 |
| 5,772,585 A | 6/1998 | Lavin et al. ................. | 600/300 |
| 5,779,634 A | 7/1998 | Ema et al. ................... | 600/407 |
| 5,807,256 A | 9/1998 | Taguchi et al. .............. | 600/425 |
| 5,809,476 A | 9/1998 | Ryan ............................. | 705/2 |
| 5,911,132 A * | 6/1999 | Sloane ........................... | 705/3 |
| 5,924,074 A * | 7/1999 | Evans ........................... | 705/3 |
| 5,978,466 A * | 11/1999 | Quattrocchi .......... | 379/265.01 |
| 6,021,404 A | 2/2000 | Moukheibir ................. | 706/46 |
| 6,026,363 A | 2/2000 | Shepard ......................... | 705/3 |
| 6,084,510 A * | 7/2000 | Lemelson et al. ...... | 340/539.13 |
| 6,085,510 A * | 7/2000 | McDonnell .................. | 56/298 |
| 6,088,695 A * | 7/2000 | Kara .................................. | 1/1 |
| 6,117,073 A * | 9/2000 | Jones et al. ................. | 600/300 |
| 6,148,297 A * | 11/2000 | Swor et al. ......................... | 1/1 |
| 6,154,731 A * | 11/2000 | Monks et al. ............. | 705/36 R |
| 6,171,237 B1 * | 1/2001 | Avitall et al. ................ | 600/300 |
| 6,212,519 B1 | 4/2001 | Segal ............................ | 707/6 |
| 6,238,337 B1 * | 5/2001 | Kambhatla et al. .......... | 600/300 |
| 6,247,004 B1 | 6/2001 | Moukheibir ................. | 706/46 |
| 6,267,722 B1 | 7/2001 | Anderson et al. ........... | 600/300 |
| 6,277,071 B1 * | 8/2001 | Hennessy et al. ........... | 600/300 |
| 6,385,589 B1 * | 5/2002 | Trusheim et al. .............. | 705/2 |
| 6,511,424 B1 * | 1/2003 | Moore-Ede et al. ......... | 600/300 |
| 7,024,370 B2 * | 4/2006 | Epler et al. ..................... | 705/3 |
| 2001/0023419 A1 | 9/2001 | LaPointe et al. ............. | 706/15 |
| 2001/0034615 A1 | 10/2001 | Wilkinson et al. ............. | 705/2 |

(Continued)

FOREIGN PATENT DOCUMENTS

EP 0286456 10/1988 ....................... 5/2

(Continued)

Primary Examiner—Gerald J. O'Connor
Assistant Examiner—Amber Altschul
(74) Attorney, Agent, or Firm—Bourque & Associates, P.A.

(57) ABSTRACT

An infectious disease surveillance system is disclosed, which comprises a database system for storing data relating to at least one infectious disease; input means for providing data to the database system; a complex adaptive system associated with the database system; processing means for processing the data of the database system and converting the data into surveillance data; and output means for displaying the surveillance data.

28 Claims, 2 Drawing Sheets

U.S. PATENT DOCUMENTS

2001/0047125 A1    11/2001   Quy ........................... 600/300

FOREIGN PATENT DOCUMENTS

| | | | |
|---|---|---|---|
| EP | 0616290 | 2/1994 | .................... 15/42 |
| EP | 0973116 | 1/2000 | |
| WO | WO 9519604 | 7/1995 | |
| WO | WO 9524010 | 9/1995 | |
| WO | WO 9706499 | 2/1997 | |
| WO | WO 9729447 | 8/1997 | |
| WO | WO 9952025 | 4/1999 | |
| WO | WO 9939298 | 8/1999 | |
| WO | WO 0007131 | 2/2000 | |
| WO | WO 0049549 | 8/2000 | .................... 17/60 |
| WO | WO 0057264 | 9/2000 | |
| WO | WO 0070529 | 11/2000 | |
| WO | WO 0126026 | 4/2001 | |
| WO | WO 0148652 | 7/2001 | .................... 17/60 |
| WO | WO 0150330 | 7/2001 | |
| WO | WO 0165449 | 9/2001 | .................... 17/60 |
| WO | WO 0169500 | 9/2001 | .................... 17/60 |
| WO | WO 0169513 | 9/2001 | |
| WO | WO 0169515 | 9/2001 | |
| WO | WO 0173427 | 10/2001 | .................... 33/48 |
| WO | WO02061647 | 8/2002 | .................... 17/60 |

* cited by examiner

FIG. 1

INFECTIOUS DISEASE SURVEILLANCE SYSTEM

FIELD OF INVENTION

The present invention relates to an infectious disease surveillance system

More particularly, the invention relates to an infectious disease surveillance system for identifying, studying the effect of and combating infectious diseases.

BACKGROUND TO INVENTION

Infectious diseases are defined as unhealthy conditions of the body or part thereof or the mind, which are caused by microorganisms such as bacteria, to viruses, rickettsiae, chlamydiae, mycoplasmas, fungi and protozoa. These microorganisms live on the skin, in the oral cavity, in the respiratory and gastrointestinal tracts, and in the genitalia, where they constitute normal flora. The interactions between the human hosts and pathogenic organisms are complex and dynamic and these interactions determine whether or not the microorganism remains apart from the human host, becomes part of the normal flora, or invades the host and causes disease.

According to the tissue tropism phenomenon, microorganisms selectively colonize specific body sites. These are called normal microbial flora and includes resident flora (which re-establishes itself if disturbed) and transient flora (which does not permanently establish itself). Commensal and symbiotic flora consists predominantly of bacteria and fungi. Furthermore, environmental factors including diet, sanitary conditions, air pollution and hygienic habits influence the species that constitute the normal microbial flora.

The host body is provided with various defence mechanism determining whether or not an infection will result, and these defence mechanisms include
1. natural barriers (e.g. skin and mucous membranes),
2. non-specific immune response factors (e.g. phagocytic cells, i.e. neutrophils and macrophages, and their products), and
3. specific immune response factors (e.g. antibodies).

Only a small proportion of the microorganisms to which humans are exposed, produce infection and disease. This pathogenesis of infection includes:
1. toxins released by micro-organisms for interacting with host cells;
2. virulence factors for assisting host invasion and resist host defence mechanisms;
3. microbial adherence, i.e. the binding to surfaces to establish a base from which tissue penetration or cellular invasion is launched, and
4. viral virulence factors contribute to initiation and propagation of infection by viruses.

The manifestations of infection include fever and systemic responses. Fever is defined as an elevation of body temperature above the normal daily variation, and includes pyrogens, febrile response, fever of unknown origin (FUO). Systemic responses are responses in various organ systems of the host as a result of an infection, and include hermatologic manifestations, cardiopulmonary manifestations, renal manifestations, hepatic manifestations, gastrointestinal manifestations, neurologic manifestations, endocrinologic and metabolic manifestations. The above facilitate the diagnosis of infections.

In order to prevent infections, the epidemiologic properties of the disease, the mode of transmission of the disease, and susceptibility of people to the disease have to be understood. In addition, immunobiologic agents are provided in the form of vaccinations, which include antigens or antibodies. Anti-infective pharmaceutical preparations are classified as antibacterial, antiviral, and anti-fungal drugs.

Combating of infectious diseases includes surveillance, analysis and control of the infectious diseases and in order to be effective, information is required to enable informed decisions by public health authorities, health and pharmaceutical researchers, politicians and persons infected by an infectious disease.

The acquisition of information is complicated due to various factors, such as lack of data, unreliable data as a result of manipulation and secrecy by governments, means for identifying relationships between acquired data, the complexity and non-linearity of infective transmission systems, the interactions between various diseases (infectious and non-infectious), the interactions between pharmaceuticals administered to combat infectious diseases, the epidemic nature of specific infectious disease, the vast number of factors influencing the working and spreading of infectious diseases, and the influence of legal issues such as patent protection of pharmaceuticals.

WO01/73427 discloses a method for analysing an infectious disease using computer based simulation engines, and includes the steps of simulating transmission of the infections disease using a first computer-based model and simulating the transmission of the infections disease using a second computer-based model. The method further includes the steps of analysing the transmission of the infections disease as a function of the first and second computer-based simulation engines.

US Patent Application 2001/0047125 A1 provides a method and apparatus for a wireless health monitoring system for interactively monitoring a disease or health condition of a patient by connecting an internet-enabled wireless web device to a health monitoring device which may be a medical device or other health related device such as an exercise machine. However, this is limited to the disease or health condition of a single patient and limited to a medical device or other health device.

It is an object of the invention to suggest an infectious disease surveillance system for identifying, studying the effects of and combating infectious diseases.

SUMMARY OF INVENTION

According to the invention, an infectious disease surveillance system, comprises
(a) a database system for storing data relating to at least one infectious disease;
(b) input means for providing data to the database system;
(c) a complex adaptive system associated with the database system;
(d) processing means for processing the data of the database system and converting the data into surveillance data; and
(e) output means for displaying the surveillance data.

The complex adaptive system may be capable of adapting according to the data provided by the input means the surveillance data, and characteristics of the input means providing the data, such as geographical location and type of input means.

The complex adaptive system may comprise at least one of the elements selected from the group comprising a Bayesian network, a neural network, a genetic algorithm and an artificial life system.

The infectious disease surveillance system may be deployed in a distributed environment, such as the Internet.

The infectious disease surveillance system may comprise decision-making means for making decisions based on the surveillance data.

The input means may be remote from the database system.

The input means may be mobile.

The input means may be connected real-time to the database system.

The database may comprise real-time data.

The infectious disease surveillance system may require an identification code for transferring data from the input means to the database system.

The infectious disease surveillance system may comprise filtering means for filtering data received from the input means.

The infectious disease may be an epidemic disease.

The infectious disease surveillance system may comprise data selected from the group comprising incidence data, prevalence data, death data, diagnosed data, estimated data, extrapolated data and predicted data.

The estimated data, extrapolated data and predicted data may be obtained by means of a model associated with the complex adaptive system and selected from the group comprising an analytical model and an empirical model.

Parameters of the model may be continuously adapted.

The infectious disease surveillance system may comprise pharmaceutical data relating to any one selected from the group comprising genetic differences of patients infected with the infectious disease, pharmaceutical interactions, pharmaceutical-disease interactions, effects of placebos, and pharmaceutical treatment compliance.

The infectious disease surveillance system may comprise constraint data relating to the infectious disease and methods for combating the infectious disease.

The database system may comprise data selected from the group comprising biological data of the infectious disease, data relating to combating of the infectious disease, and data relating to interactions of intellectual property factors and combating methods of the infectious disease.

The infectious disease surveillance system may comprise data relating to any one selected from the group comprising classification of diseases, history of diseases, origins of diseases, functioning and pathogenesis of diseases, symbiotic infections, commensal infections, parasitic infections, causes of diseases, transmission modes of diseases, susceptibility of people to diseases, frequency of diseases, severity of diseases, impact of diseases, duration of diseases, duration of infection with diseases, symptoms of diseases, diagnosis of diseases, interactions of diseases, epidemic nature of diseases, defence mechanism of organisms to combat diseases, immunodeficiency diseases, primary immunodeficiency diseases, secondary immunodeficiency diseases, congenital immunodeficiency diseases, acquired immunodeficiency diseases, allergic reactions, sexually transmitted diseases, immune system of organisms, viral infections, and non-infectious diseases.

The infectious disease may be an immunodeficiency disease.

The immunodeficiency disease may be classified according to any one selected from the group comprising low antibody levels, impaired functioning of white blood cells due to T-lymphocyte problems, T-lymphocyte problems, B-lymphocyte problems, killing and malfunctioning of white blood cells, abnormal white blood cell movement, and abnormal complement system.

Data of the database system may be systemized into characteristics of an infected person infected with the infectious disease.

The infectious disease surveillance system may comprise anonymity means for ensuring anonymity of the infected person.

Data of the database system may be systemised into any one selected from the group comprising geographical regions, characteristics of geographical regions, and characteristics of a geographical region associated with a patient infected with the infectious disease.

Data of the database system may incorporate data of people infected with the infectious disease, data of people ill with the disease, and data of people who have died of the disease.

The infectious disease surveillance system may comprise a mathematical model for determining data of people infected with the infectious disease, data of people ill with the infectious disease, and data of people who have died of the infectious disease.

The mathematical model may be a function of time.

The relationships of data of people infected with the infectious disease, data of people ill with the infectious disease, and data of people who have died of the infectious disease may be compared.

The infectious disease surveillance system may be adapted for utilisation for any function selected from the group comprising
  (a) detection of infectious diseases;
  (b) detection of new infectious diseases;
  (c) detection of new non-infectious diseases;
  (d) prediction of the impact of a disease;
  (e) prediction of the impact of a disease as a function of time;
  (f) evaluation of infectious disease combating methods;
  (g) providing information for combating infectious diseases;
  (h) obtaining trends relating to infectious diseases;
  (i) making predictions relating to infectious diseases;
  (j) evaluating effectiveness of pharmaceutical preparations;
  (k) detection of virus resistance;
  (l) determining mode of transmission of infectious diseases;
  (m) determining susceptibility of people to infectious diseases;
  (n) evaluation of the impact of the infectious disease on sustainable development; and
  (o) predicting the impact of the infectious disease on sustainable development.

The infectious disease combating methods may comprise any one selected from the group comprising clinical objectives, virologic objectives, immunologic objectives, epidemiologic objectives, eradication of the infectious disease, prevention of infection with the infectious disease, treatment of patients infected with the infectious disease, development of a vaccine for the infectious disease, development of a cure for the infectious disease, maximum sustained suppression of effects of the infectious disease, immune stimulation of a patient infected with the infectious disease, and achieving long-term effectiveness of pharmaceutical preparation for treating patients infected with the infectious disease.

Also according to the invention, a method of surveying an infectious disease, which comprises the steps of
  (a) providing a database system for storing data relating to at least one infectious disease;
  (b) providing a complex adaptive system associated with the database system;

(c) providing data to the database system;
(d) processing the data of the database system;
(e) converting the data into surveillance data; and
(f) displaying the surveillance data.

The method may be adapted for utilisation for any function selected from the group comprising:
(a) detecting infectious diseases;
(b) detecting new infectious diseases;
(c) detecting new non-infectious diseases;
(d) predicting the impact of a disease;
(e) predicting the impact of a disease as a function of time;
(f) evaluating infectious disease combating methods;
(g) providing information for combating infectious diseases;
(h) obtaining trends relating to infectious diseases,
(i) making predictions relating to infectious diseases;
(j) evaluating effectiveness of pharmaceutical preparations;
(k) detecting virus resistance,
(l) determining mode of transmission of infectious diseases;
(m) determining susceptibility of people to infectious diseases;
(n) evaluating the impact of the infectious disease on sustainable development; and
(o) predicting the impact of the infectious disease on sustainable development.

BRIEF DESCRIPTION OF DRAWINGS

The invention will now be described by way of example with reference to the accompanying schematic drawings.

In the drawings there is shown in.

DETAILED DESCRIPTION OF DRAWINGS

Figure 1:
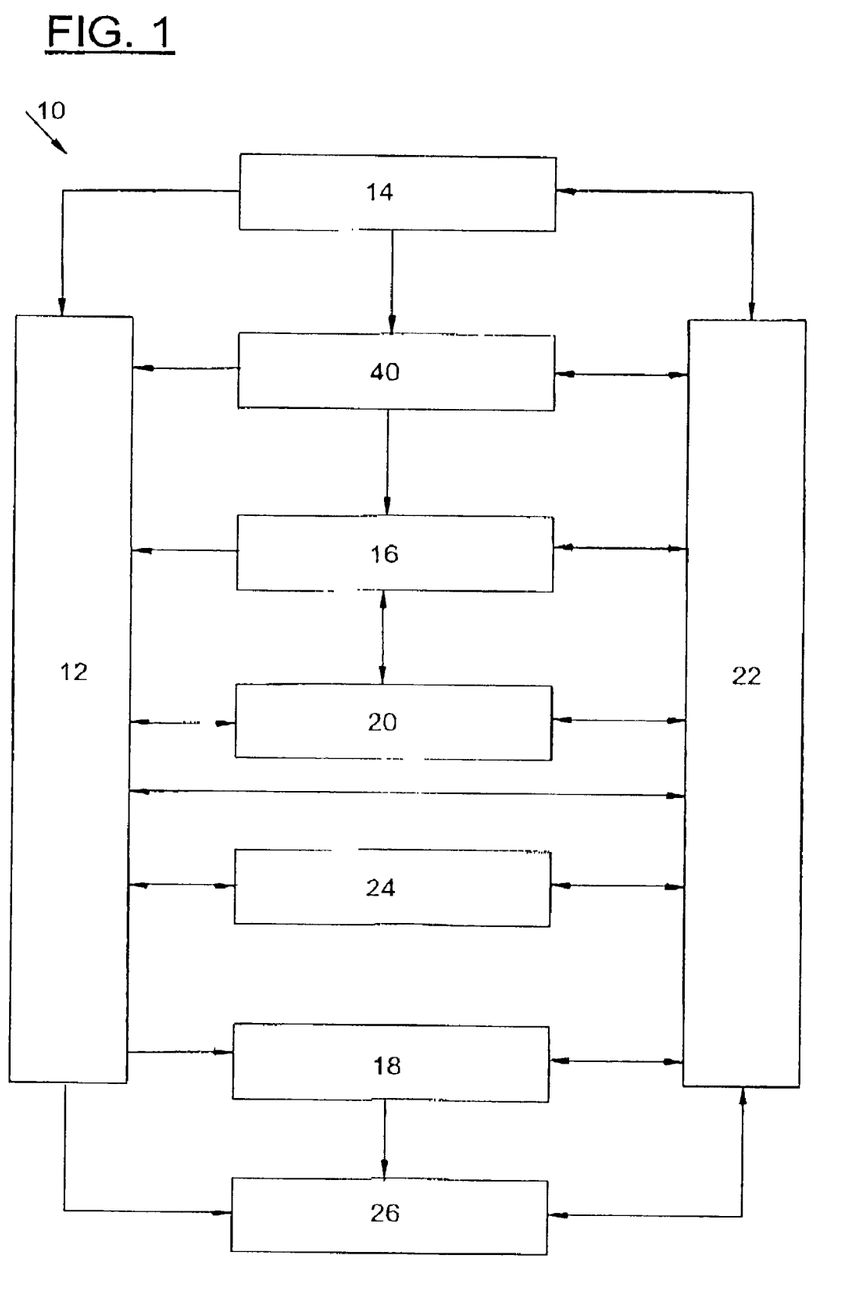
FIG. 1 a schematic diagram of an infectious disease surveillance system in accordance with the invention.
Figure 2:
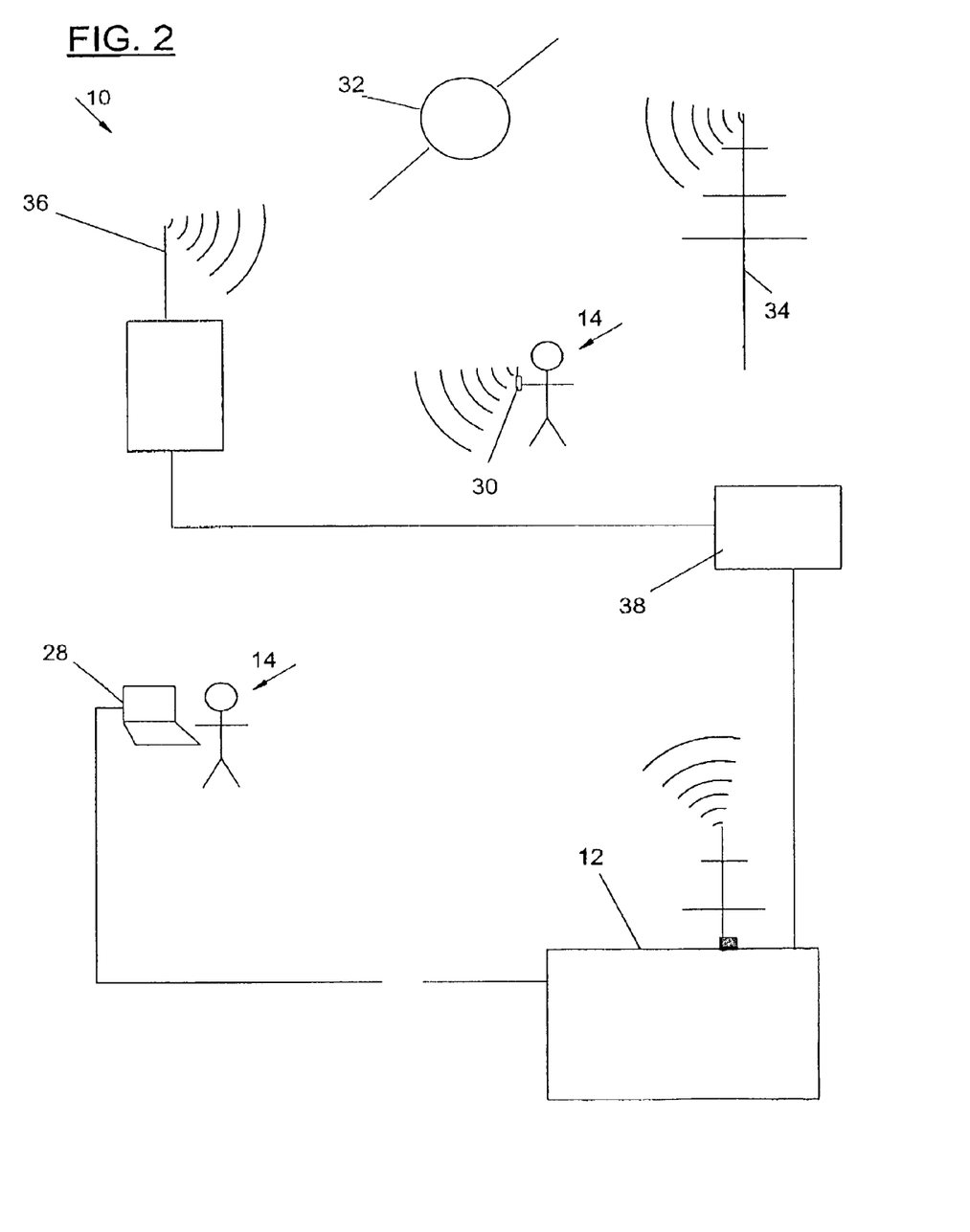
FIG. 2 deployment of the infectious disease surveillance system shown in FIG. 1.

Referring to FIGS. 1 and 2, an infectious disease surveillance system in accordance with the invention, generally indicated by reference numeral 10, comprises a database system 12 for storing data relating to at least one infectious disease, input means 14 for providing data to the database system 12, processing means 16 for processing the data of the database system 12 and converting the data into surveillance data, and output means 18 for displaying the surveillance data. The processing means 16 is further associated with a mathematical model 20.

The infectious disease surveillance system 10 comprises a complex adaptive system 22 which acquires information about its environment, in this example the input means 14, data from the input means 14, its own interaction with the environment, data in the database 12 and the processing means 16 in processing the data, identifying regularities in the information, in this example data in the database 12, data from the input means 14 and data acquired from the mathematical model 20, condensing these regularities into a kind of schema or complex adaptive model 24, to enable action and decision-making based on the complex adaptive model 24.

The complex adaptive system 22 is associated with a Bayesian network, a neural network, a genetic algorithm or an artificial life system. The complex adaptive system 22 is deployed in a distributed environment, such as the Internet.

The infectious disease surveillance system 10 furthermore comprises decision making means 26 for assisting and making decisions based on the surveillance data and which decision-making means 26 interacts with the complex adaptive model 24 and surveillance data. The decision-making means 26 are of electronic or human nature.

In FIG. 2, the infectious disease surveillance system 10 is shown deployed whereby the input means 14 include computer terminals 28 and mobile communication devices 30 which are remote from the database system 12. The computer terminals 28 are in some instances mobile and communicate via a satellite 32 or communication towers 34 and 36 with the database system 12. The input means 14 in some instances communicates via the Internet 38 with the database system 12. By means of the various communication means the input means 14 are connected real-time to the database system 12. Thus, some of the data in the database system 12 is real-time data. Thus medical aid workers and doctors in remote areas such as central Africa can provide real-time data to the database system 12 via mobile communication devices 30. This enables early detection of new infectious diseases and the spread of infectious diseases.

The infectious disease surveillance system 10 requires an identification code for transferring data from the input means 14 to the database system 12. Filtering means 40 for filtering the data received from the input means 14 may also be provided. This ensures reliability of the data and adjustment of data to ensure correctness.

The infectious disease(s) is generally an epidemic disease, but may also includes non-infectious diseases. The infectious diseases may relate to animals, in particular primates.

The database system 12 includes incidence data, prevalence data, and death data relating to the infectious disease(s). The data comprises diagnosed, estimated, extrapolated and predicted data. The diagnosed data is acquired from the input means 14, while the estimated, extrapolated and predicted data are obtained by means of the mathematical model 20 or the complex adaptive model 24. The mathematical model 20 comprises an analytical/or an empirical model.

The mathematical model 20 and complex adaptive model 24 may comprise parameters which are continuously adapted and improved by the processing means 16 utilising data from the database system 12, the input means 14, and estimated, extrapolated and predicted data or improved by the complex adaptive system 22.

The surveillance data provides information for evaluating
(a) trends and predictions relating to the infectious disease(s);
(b) infectious disease combating methods; and
(c) the impact of the infectious disease.

The impact of the infectious disease is classified according to socio-environmental impact, legal impact, epidemiological impact, demographic impact, economic impact and impact on development, including sustainable development.

The decision-making means 26 generally relate to policies regarding governance, research, social activities, and legal issues. The research is generally based on social science, law, politics and medicine.

The infectious disease combating methods comprise:
(a) clinical objectives,
(b) virologic objectives,
(c) immunologic objectives, and
(d) epidemiologic objectives.

The infectious disease combating methods comprise primary objectives and secondary objectives. The primary objectives include:
(a) eradication of the infectious disease,
(b) prevention of infection with the infectious disease, and (c) treatment of patients infected with the infectious disease.

The secondary objectives include:
(a) development of a vaccine for the infectious disease,
(b) development of a cure for the infectious disease,
(c) maximum sustained suppression of effects of the infectious disease,
(d) immune stimulation of a patient infected with the infectious disease, and
(e) achieving long-term effectiveness of pharmaceutical preparation for treating patients infected with the infectious disease.

The prevention of infection with the infectious disease includes sex abstinence, protected sex, no blood and organ donation, avoidance of pregnancy, notification of sexual partners of acquired diseases, correct utilisation and disposal of needles, pharmaceutical treatment programs, protection mechanisms where contact with body fluids are possible, and immunizations.

The treatment of patients infected with the infectious disease incorporates antibacterial pharmaceuticals, antiviral pharmaceuticals, anti-fungal pharmaceuticals, anti-retroviral pharmaceuticals, and immune based therapy pharmaceuticals. The data of the database system 12 comprises pharmaceutical data relating to genetic differences of patients infected with the infectious disease pharmaceutical interactions, pharmaceutical-disease interactions, effects of placebos, and pharmaceutical treatment compliance. The antiretroviral pharmaceuticals are classified according to any one selected from the group comprising fusion inhibitors, non-nucleoside reverse transcriptase inhibitors, nucleoside and nucleotide analogs, protease inhibitors, and ribonucleotide reductase inhibitors. The immune based therapy pharmaceuticals are classified according to any one selected from the group comprising cytokines, immuno-therapeutics, and TNF inhibitors.

The database system 12 comprises constraint data relating to the infectious disease and methods for combating the infectious disease. The constraint data are classified according to infectious disease eradication constraints, infectious disease treatment constraints, and infectious disease prevention constraints, and classified according to limited information, access to information, intellectual property factors relating to pharmaceuticals and treatment of diseases, cost factors, time factors, organisational factors, and infrastructure.

The infectious disease surveillance system 10 comprises the following subsystems:
(a) infectious disease subsystem comprising biological data of the infectious disease,
(b) infectious disease combating subsystem comprising data relating to the combating of the infectious disease, and
(c) intellectual property subsystem comprising data relating to interactions of intellectual property factors and combating methods of the infectious disease.

The data of the database 12 can relate to classification of diseases, history of diseases, origins of diseases, functioning and pathogenesis of diseases, symbiotic infection, commmensal infection, parasitic infection, causes of diseases, transmission modes of diseases, susceptibility of people to diseases, frequency of diseases, severity of diseases, impact of diseases, duration of diseases, duration of infection with diseases, symptoms of diseases, diagnosis of diseases, interactions of diseases, epidemic nature of diseases, defence mechanism of organisms to combat diseases, immunodeficiency diseases, primary immunodeficiency diseases, secondary immunodeficiency diseases, congenital immunodeficiency diseases, acquired immunodeficiency diseases, allergic reactions, sexually transmitted diseases, immune system of organisms, and viral infections.

The infectious disease may be an immunodeficiency disease and be classified according to low antibody levels, impaired functioning of white blood cells due to T-lymphocyte problems, T-lymphocyte problems, B-lymphocyte problems, killing and malfunctioning of white blood cells, abnormal white blood cell movement, and abnormal complement system. The infectious disease may be an immunodeficiency disease, namely common variable immunodeficiency, selective antibody deficiency, transient hypogammaglobulinemia of infancy, X-linked agammaglobulinemia (Bruton's agammaglobulinemia), Chronic mucocutaneous candidiasis, DiGeorge anomaly, Ataxia-telangiectasia, Severe combined immunodeficiency disease, Wiskott-Aldrich syndrome, X-linked lymphoproliferative syndrome, Human Immunodeficiency Virus, Chédiak-Higashi syndrome, Chronic granulomatous disease, Leukocyte glucose-6-phosphate dehydrogenase deficiency, Myeloperoxidase, Hyperimmunoglobulinemia E (Job-Buckles syndrome), Leukocyte adhesion defect, Complement component 3 (C3) deficiency, Complement component 6 (C6) deficiency, Complement component 7 (C7) deficiency, and Complement component 8 (C8) deficiency.

The viral infections are classified according to immunodeficiency viral infections, respiratory viral infections, herpes viral infections, central nervous system viral infections, arbovirus infections, arenavirus infections, and hantavirus infections. The viral infections are selected from the group comprising human immunodeficiency virus, common cold, influenza, herpes simplex, shingles, infectious mononucleosis, rabies, Creutzfeld-Jacob disease, Progressive multifocal leukoencephalpathy, Tropical spastic paraparesis, Arbovirus encephalitis, lymphocytic choriomeningetis, and Hemorrhagic fevers.

The sexually transmitted diseases are classified according to traditional sexually transmitted diseases, modern sexually transmitted diseases, and occasional sexually transmitted diseases. The sexually transmitted diseases are selected from the group comprising chancroid, Gonorrhoea, Granuloma inguinale, Lymnphogranuloma venereum, Syphilis, Chlamydial cervicitus, Crabs (lice, pendiculosis pubis), Genital candidiasis, Genital herpes, Genital warts, Human immunodeficiency virus infections, Molluscum contaglosum, Nongonococcal urethritis, Scabies, Trichomoniasis, Amebiasis, Campylobacteriosis, Cytomegalovirus infections, Giardiasis, Hepatitis A, Hepatitis B, Salmonellosis, and Shigellosis.

The data of the database system 12 comprises intellectual property data relating to pharmaceutical patents, patent legislation, unfair competition, parallel importation and THRIPS. The intellectual property data is classified into continents, regions or states.

Data from the input means 14 is systemised into characteristics of an infected person infected with the infectious disease and includes diagnostic data of patients. The surveillance data is systemised into patient characteristics of a patient infected with the infectious disease. The infectious disease surveillance system 10 comprises anonymity means for ensuring the anonymity of the patient. The patient characteristics are selected from the group comprising age of the patient, sex of the patient, physical characteristics of the patient, domicilium of the patient, geographical location where the infectious disease was acquired by the patient, type of location where the infectious disease was acquired by the patient, manner in which infectious disease was acquired by the patient, marital status of the patient, sexual activities of the patient, health of the patient, movements of the patient, mobility of the patient, income of the patient, ethnicity of the patient, nationality of the patient, language(s) of the patient, education of the patient, and occupation of the patient.

The input data and the surveillance data are systemised into characteristics of a geographical region associated with patients infected with the infectious disease or the patient characteristics are systemised into characteristics of a geographical region associated with the patient or only the input data and the surveillance data are systemised into geographical regions. The data of the database system 12 may includes characteristics of the geographical regions and which are selected from the group comprising continent, state, total population, annual population growth rate, urban population, population under age 15, population aged 65 and above, total fertility rate per woman, GDP index, GDP per capita, GDP per capita annual growth rate, GDP per capita highest value, Year of GDP per capita highest value, Average annual change in consumer price index, Gini index, HDI (Human Development Index) value, HDI (Human Development Index) trends, GDP per capita rank minus HDI (Human Development Index) rank, Infant mortality rate, Under-five mortality rate, Life expectancy at birth, Life expectancy index, Probability at birth of surviving to age 65, Maternal mortality ratio reported, Adult literacy rate, Adult illiteracy rate, Combined primary, secondary and tertiary gross enrolment ratio, Human poverty index (HPI-1) rank, Human poverty index (HPI-1) value, Population not using improved water sources, Underweight children under age five, Income poverty rank, Population below income poverty line of national poverty line, Human poverty index (HPI-1) rank minus income poverty rank, Human poverty index (HPI-2) rank, Human poverty index (HPI-2) value, Probability at birth of not surviving to age 60, People lacking functional literacy skills, Human poverty index (HPI-2) rank minus income poverty rank, Population using adequate sanitation facilities, Population with access to essential drugs, One-year olds fully immunized against specific diseases, Oral rehydration therapy use rate, Contraceptive prevalence, Births attended by skilled health staff, number of Physicians, Public health expenditure, Private health expenditure, Per capita health expenditure, Undernourished people, Children underweight for age, Children under height for age, Infants with low birth-weight, Cigarette consumption per adult, Tuberculosis cases, Malaria cases, Public education expenditure, Tertiary students in science, mathematics and engineering courses, Military expenditure, Imports of goods and services, Exports of goods and services, Primary exports, Manufactured exports, High-technology exports, Terms of trade, Net official development assistance (ODA) disbursed, ODA per capita of donor country, ODA to least developed countries, Net grants by NGOs, ODA received, Net foreign direct investment flows, Total debt service as percentage of GDP, Total debt service as percentage of exports of goods and services, Unemployed people, Unemployment rate, Average annual unemployment rate, Female unemployment rate as % of male unemployment rate, Youth unemployment rate, Female youth unemployment rate as % of male youth unemployment rate, Long-term unemployment, Traditional fuel consumption, Electricity consumption per capita, GDP per unit of energy consumption, Carbon dioxide emissions share of world total, Carbon dioxide emissions per capita, Internally displaced people, Refugees, Refugees by county of asylum, Refugees by country of origin, Conventional arms transfers, Total armed forces, Total crime, Sexual assault, Assault, Gender-related development index (GDI), HDI rank minus GDI rank, Gender empowerment measure (GEM) rank, Gender empowerment measure (GEM) value, Ratio of estimated female to male earned income, Female economic activity rate, and Contributing family workers.

The data of the database system 12 incorporates data of people infected with the infectious disease, data of people ill with the disease, and data of people who have died of the disease. The mathematical model 20 comprises mathematical formulations for determining the data of people infected with the infectious disease, data of people ill with the disease, and data of people who have died of the disease. The mathematical model 20 is generally a function of time.

The infectious disease surveillance system 10 may be utilised
(a) to detect new infectious diseases,
(b) to determine the impact of infectious diseases as a function of time,
(c) to determine the effective of pharmaceutical preparations,
(d) to detect mutation of viruses, and
(e) to determine the relationship between infectious diseases and sustainable development.

The invention claimed is:

1. An infectious disease surveillance system, which comprises:
   (a) a database system for storing data relating to at least one infectious disease;
   (b) input means for providing biological data to the database system, said input means being remote from the database system and configured to be mobile;
   (c) computer processing means associated with the database system and for processing biological data of the database system and converting the processed data into surveillance data;
   (d) a computational complex adaptive system being operatively associated with the computer processing means and being associated with the database system, the complex adaptive system configured for adapting continuously according to the biological data provided by the input means and the surveillance data;
   (e) at least one model selected from the group comprising an analytical model and an empirical model associated with the complex adaptive system, the model having parameters which are capable of being continuously adapted;
   (f) output means for displaying the surveillance data generally instantly after said input means provides said biological data to said database system; and
   (g) decision-making means, responsive to said surveillance data, for making policy decisions regarding the surveillance data.

2. A system as claimed in claimed 1, in which the complex adaptive system is capable of adapting according to characteristics of the input means providing the data.

3. A system as claimed in claimed 1, in which the complex adaptive system comprises at least one of the elements selected from the group comprising a Bayesian network, a neural network, a genetic algorithm and an artificial life system.

4. A system as claimed in claimed 1, which is deployed in a distributed environment.

5. A system as claimed in claimed 1, in which the input means are connected real-time to the database system.

6. A system as claimed in claimed 1, in which the database comprises real-time data.

7. A system as claimed in claimed 1, which requires an identification code for transferring data from the input means to the database system.

8. A system as claimed in claimed 1, which comprises filtering means for filtering data received from the input means.

9. A system as claimed in claimed 1, in which the infectious disease is an epidemic disease.

10. A system as claimed in claimed 1 which comprises data selected from the group comprising incidence data, prevalence data, death data, diagnosed data, estimated data, extrapolated data and predicted data.

11. A system as claimed in claimed 10, in which the estimated data, extrapolated data and predicted data are obtained by means of the model.

12. A system as claimed in claim 1, which comprises pharmaceutical data relating to any one selected from the group comprising genetic differences of patients infected with the infectious disease, pharmaceutical interactions, pharmaceutical-disease interactions, effects of placebos, and pharmaceutical treatment compliance.

13. A system as claimed in claim 1, which comprises constraint data relating to the infectious disease and methods for combating the infectious disease.

14. A system as claimed in claimed 13, in which the infectious disease combating methods comprise any one selected from the group comprising clinical objectives, virologic objectives, immunologic objectives, epidemiologic objectives, eradication of the infectious disease, prevention of infection with the infectious disease, treatment of patients infected with the infectious disease, development of a vaccine for the infectious disease, development of a cure for the infectious disease, maximum sustained suppression of effects of the infectious disease, immune stimulation of a patient infected with the infectious disease, and achieving long-term effectiveness of pharmaceutical preparation for treating patients infected with the infectious disease.

15. A system as claimed in claim 1, in which the database system comprises data selected from the group comprising biological data of the infectious disease, data relating to combating of the infectious disease, and data relating to interactions of intellectual property factors and combating methods of the infectious disease.

16. A system as claimed in claim 1, which comprises data relating to any one selected from the group comprising classification of diseases, history of diseases, origins of diseases, functioning and pathogenesis of diseases, symbiotic infections, commensal infections, parasitic infections, causes of diseases, transmission modes of diseases, susceptibility of people to diseases, frequency of diseases, severity of diseases, impact of diseases, duration of diseases, duration of infection with diseases, symptoms of diseases, diagnosis of diseases, interactions of diseases, epidemic nature of diseases, defence mechanism of organisms to combat diseases, immunodeficiency diseases, primary immunodeficiency diseases, secondary immunodeficiency diseases, congenital immunodeficiency diseases, acquired immunodeficiency diseases, allergic reactions, sexually transmitted diseases, immune system of organisms, viral infections, and non-infectious diseases.

17. A system as claimed in claim 1, in which the infectious disease is an immunodeficiency disease.

18. A system as claimed in claim 17, in which the immunodeficiency disease is classified according to any one selected from the group comprising low antibody levels, impaired functioning of white blood cells due to T-lymphocyte problems, T-lymphocyte problems, B-lymphocyte problems, killing and malfunctioning of white blood cells, abnormal white blood cell movement, and abnormal complement system.

19. A system as claimed in claim 1, in which data of the database system is systemized into characteristics of an infected person infected with the infectious disease.

20. A system as claimed in claim 19, which comprises anonymity means for ensuring anonymity of the infected person.

21. A system as claimed in claim 1, in which data of the database system is systemised into any one selected from the group comprising geographical regions, characteristics of geographical regions, and characteristics of a geographical region associated with a patient infected with the infectious disease.

22. A system as claimed in claim 1, in which data of the database system incorporates data of people infected with the infectious disease, data of people ill with the disease, and data of people who have died of the disease.

23. A system as claimed in claim 1, which comprises a mathematical model for determining data of people infected with the infectious disease, data of people ill with the infectious disease, and data of people who have died of the infectious disease.

24. A system as claimed in claim 23, in which the mathematical model is a function of time.

25. A system as claimed in claim 23, in which the relationships of data of people infected with the infectious disease, data of people ill with the infectious disease, and data of people who have died of the infectious disease are compared.

26. A system as claimed in claim 1, adapted for utilisation for any function selected from the group comprising
(a) detection of infectious diseases;
(b) detection of new infectious diseases;
(c) detection of new non-infectious diseases;
(d) prediction of the impact of a disease;
(e) prediction of the impact of a disease as a function of time;
(f) evaluation of infectious disease combating methods;
(g) providing information for combating infectious diseases;
(h) obtaining trends relating to infectious diseases;
(i) making predictions relating to infectious diseases;
(j) evaluating effectiveness of pharmaceutical preparations;
(k) detection of virus resistance;
(l) determining mode of transmission of infectious diseases;
(m) determining susceptibility of people to infectious diseases;
(n) evaluation of the impact of the infectious disease on sustainable development; and
(o) predicting the impact of the infectious disease on sustainable development.

27. A method of surveying an infectious disease, which comprises the steps of
(a) providing a database system for storing biological data relating to at least one infectious disease;
(b) providing computer processing means associated with the database system and for processing said biological data of the database system and converting the processed biological data into surveillance data;
(c) providing a computational complex adaptive system being operatively associated with the computer processing means and being associated with the database system,
(d) providing at least one model associated with the complex adaptive system, the model being selected from the group comprising an analytical model and an empirical model;

(e) continuously adapting the parameters of the model;
(f) providing biological data to the database system by an input means configured to be mobile and being remote from the database system;
(g) processing the biological data of the database system;
(h) converting the biological data into surveillance data;
(i) continuously adapting the complex adaptive system according to the biological data provided to the database system and the surveillance data; and
(j) displaying the surveillance data generally instantly after said input means provides said biological data to said database system.

28. A method as claimed in claim 27, which is adapted for utilisation for any function selected from the group comprising:

(a) detecting infectious diseases;
(b) detecting new infectious diseases;
(c) detecting new non-infectious diseases;
(d) predicting the impact of a disease;
(e) predicting the impact of a disease as a function of time;
(f) evaluating infectious disease combating methods;
(g) providing information for combating infectious diseases;
(h) obtaining trends relating to infectious diseases;
(i) making predictions relating to infectious diseases;
(j) evaluating effectiveness of pharmaceutical preparations;
(k) detecting virus resistance;
(l) determining mode of transmission of infectious diseases;
(m) determining susceptibility of people to infectious diseases;
(n) evaluating the impact of the infectious disease on sustainable development; and
predicting the impact of the infectious disease on sustainable development.

* * * * *